US00PP31668P3

(12) United States Plant Patent
Gebhardt

(10) Patent No.: US PP31,668 P3
(45) Date of Patent: Apr. 14, 2020

(54) ***EUTROCHIUM* PLANT NAMED 'FLOREUPRE1'**

(50) Latin Name: ***Eutrochium purpureum* (syn. *Eupatorium purpureum*)**
Varietal Denomination: FLOREUPRE1

(71) Applicant: Florensis B.V., Hendrik-Ido-Ambacht (NL)

(72) Inventor: Ute Gebhardt, Quedlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days.

(21) Appl. No.: 16/602,016

(22) Filed: Jul. 19, 2019

(65) Prior Publication Data

US 2020/0037487 P1 Jan. 30, 2020

Related U.S. Application Data

(60) Provisional application No. 62/764,307, filed on Jul. 27, 2018.

(51) Int. Cl.
*A01H 5/02* (2018.01)
*A01H 6/14* (2018.01)
*A01H 6/00* (2018.01)

(52) U.S. Cl.
USPC ..... Plt./263.1
CPC ..... *A01H 6/00* (2018.05); *A01H 5/02* (2013.01)

(58) Field of Classification Search
USPC ..... Plt./263.1
CPC ..... A01H 5/02; A01H 6/14
See application file for complete search history.

*Primary Examiner* — Annette H Para
(74) *Attorney, Agent, or Firm* — Audrey Charles

(57) ABSTRACT

A new and distinct cultivar of *Eutrochium* plant named 'FLOREUPRE1', characterized by its medium red-purple colored inflorescences, medium green-colored foliage, low growth vigor, and compact-upright growth habit, is disclosed.

1 Drawing Sheet

Latin name of genus and species of plant claimed: *Eutrochium purpureum* (syn. *Eupatorium purpureum*).
Variety denomination: 'FLOREUPRE1'.

BACKGROUND OF THE INVENTION

The present invention relates to a new and distinct cultivar of *Eutrochium* plant botanically known as *Eutrochium purpureum* and hereinafter referred to by the cultivar name 'FLOREUPRE1'.

The new cultivar originated in a controlled breeding program in Quedlinburg, Germany during August 2011. The objective of the breeding program was the development of *Eutrochium* cultivars having a compact growth habit.

The new *Eutrochium* cultivar is the result of open-pollination. The female (seed) parent of the new cultivar is the proprietary *Eutrochium purpureum* breeding selection coded 4846-1, not patented, characterized by its medium cream-rose colored ray florets, dark green-colored foliage, and vigorous, upright growth habit. The male (pollen) parent of the new cultivar is unknown. The new cultivar was discovered and selected as a single flowering plant within the progeny of the above stated open-pollination during September 2012 in a controlled environment in Quedlinburg, Germany.

Asexual reproduction of the new cultivar by terminal stem cuttings since September 2012 in Quedlinburg, Germany and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'FLOREUPRE1' as a new and distinct cultivar of *Eutrochium* plant:

1. Medium red-purple colored inflorescences;
2. Medium green-colored foliage;
3. Low growth vigor; and
4. Compact-upright growth habit.

Plants of the new cultivar differ from plants of the female parent primarily in having a different ray floret color, lower growth vigor, and a more compact growth habit.

Of the many commercially available *Eutrochium* cultivars, the most similar in comparison to the new cultivar is 'Little Joe', U.S. Plant Pat. No. 16,122. However, in side-by-side comparisons, plants of the new cultivar differ from plants of 'Little Joe' in at least the following characteristics:

1. Plants of the new cultivar are shorter than plants of 'Little Joe';
2. Plants of the new cultivar have a darker purple-colored flowers than plants of 'Little Joe'; and
3. Plants of the new cultivar have larger leaves than plants of 'Little Joe'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs may differ slightly from the color values cited in the detailed description, which accurately describes the colors of 'FLOREUPRE1'. The plants were approximately 18-months old and grown in Elburn, Ill. in one-gallon containers for approximately 5 weeks in a greenhouse and 16 months in an outdoor nursery bed in West Chicago, Ill. Plants were pinched once after transplant into the one-gallon container.

DETAILED BOTANICAL DESCRIPTION

Figure 1:
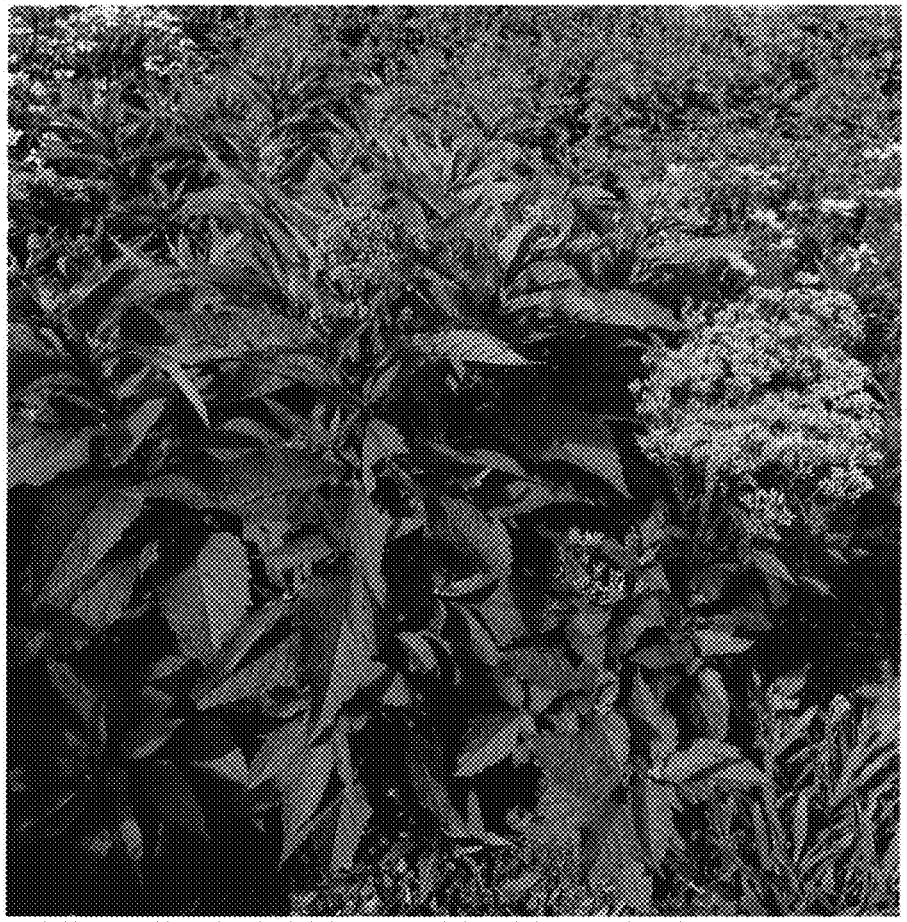
FIG. 1 illustrates a side view of the overall growth and flowering habit of 'FLOREUPRE1'.
Figure 2:
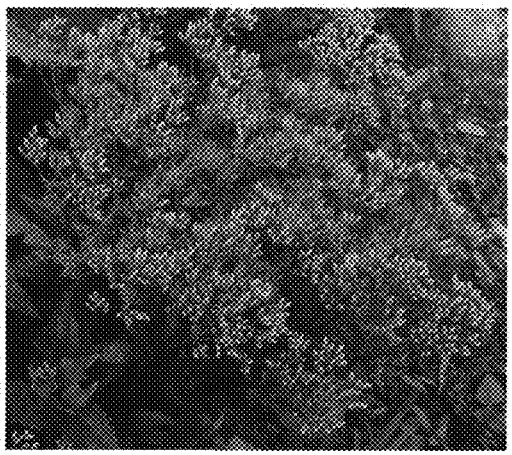
FIG. 2 illustrates a close-up view of an inflorescence of 'FLOREUPRE1'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2019 under natural light conditions in West Chicago, Ill.

The following descriptions and measurements describe approximately 18-month old plants produced from cuttings from stock plants. The plants were grown in Elburn, Ill. in a glass-covered greenhouse and transplanted into one-gallon containers for approximately 5 weeks. Plants were pinched once after transplant into the one-gallon container. No supplemental lighting was provided. Plants were then transplanted to an outdoor nursery bed in West Chicago, Ill. for approximately 16 months, which included one over-wintering period. Measurements and numerical values represent averages of typical plants.

Botanical classification: *Eutrochium purpureum* 'FLOREUPRE1'.

Parentage:

*Female parent.*—Proprietary *Eutrochium purpureum* breeding selection coded 4846-1, not patented.

*Male parent.*—Unknown.

Propagation:

*Type cutting.*—Terminal stem.

*Time to initiate roots.*—Approximately 7 to 10 days at 70° F. (21° C.).

*Time to produce a rooted cutting.*—Approximately 42 to 49 days at 70° F. (21° C.).

*Root description.*—Medium in thickness, fibrous.

*Rooting habit.*—Freely branching, dense.

Plant description:

*Commercial crop time.*—Approximately 10 to 12 weeks from a rooted cutting to finish in a 15 cm container.

*Growth habit and general appearance.*—Herbaceous perennial, low growth vigor, and compact-upright.

*Hardiness.*—USDA Zone 5a (−20° F. to −15° F./−28.9° C. to −26° C.).

*Size.*—Height from soil level to top of plant plane: Approximately 75.0 cm. Width: Approximately 70.0 cm.

*Branching habit.*—Freely branching, pinching improves lateral branching. Quantity of main branches per plant: Approximately 9.

*Stems.*—Strength: Very strong. Aspect: Nearly erect. Shape: Rounded. Length to base of inflorescence: Approximately 52.0 cm. Diameter: Approximately 1.0 cm. Length of central internode: Approximately 6.0 cm. Texture: Sparsely pubescent. Lenticels: Approximately 100 per node, with a length of approximately 1.0 to 2.0 mm and a width of less than 1.0 mm. Color of young and mature stems: 146B with a heavy overlay of 187A and lenticels of N187A.

Foliage description:

*General description.*—Form: Simple. Arrangement: Two to three per node in a single whorl.

*Leaves.*—Aspect: Acute to perpendicular to stem. Shape: Elliptic. Margin: Crenate. Apex: Acute to narrowly acuminate. Base: Attenuate. Venation pattern: Pinnate. Length of mature leaf: Approximately 16.5 cm. Width of mature leaf: Approximately 7.2 cm. Texture of upper surface: Sparsely pubescent. Texture of lower surface: Densely pubescent. Color of upper surface of young and mature foliage: Closest to 137A with 146A and venation of 146B with midvein having an overlay of 187A. Color of lower surface of young and mature foliage: Closest to 147B with venation of 146D.

*Petiole.*—Length: Approximately 2.3 cm. Diameter: Approximately 3.0 mm. Texture of upper and lower surfaces: Sparsely pubescent. Color of upper and lower surfaces: 146D with an overlay of 187A on upper surface.

Flowering description:

*Flowering habit.*—'FLOREUPRE1' is freely flowering under outdoor growing conditions blooming from early summer through autumn.

*Lastingness of individual inflorescence on the plant.*—Approximately 3 weeks.

Inflorescence description:

*General description.*—Type: Discoid, arranged in compound corymbs, persistent. Aspect: Primarily facing upward. Arrangement: Terminal, held upright on strong peduncles. Fragrance: None detected. Quantity per plant: Approximately 8. Height of corymb (including peduncle): Approximately 22.0 cm. Diameter of corymb: Approximately 26.0 cm. Height of individual head: Approximately 1.4 cm. Diameter of individual head: Approximately 1.2 cm.

*Peduncle.*—Strength: Strong. Aspect: Erect to approximately 45° from vertical. Length: Approximately 9.0 cm. Diameter: Approximately 3.0 mm. Texture: Densely pubescent with short appressed hairs. Color: 187A with lenticels of N187A.

*Bud.*—Shape: Ellipsoid. Length: Approximately 8.0 mm. Diameter: Approximately 3.0 mm. Color: NN155D with an overlay of 70A to 70B.

*Ray florets.*—Not observed.

*Disc florets.*—Quantity per head: Approximately 10. Shape: Tubular, pappus of capillary bristles, approximately 5.0 mm in length, at base of tube portion. Margin of free portion: Entire. Apex: Five acute tips. Base: Fused. Length: Approximately 1.3 cm. Diameter: Approximately 2.0 mm. Texture: Glabrous. Color of upper or inner surface when first and fully open: NN155D with an overlay of N75B. Color of lower or outer surface when first and fully open: NN155D with an overlay of N75A, base of 145C.

*Receptacle.*—Shape: Dome. Height: Approximately 0.5 mm. Diameter: Approximately 1.0 mm. Color: 146C.

*Phyllaries.*—Quantity per inflorescence Approximately 17. Arrangement: In multiple whorls. Shape: Narrowly elliptic to narrowly ovate. Margin: Entire, ciliate. Apex: Acute. Base: Truncate. Length of innermost: Approximately 7.0 mm. Length of outermost: Approximately 2.0 mm. Width of all: Approximately 1.0 mm to 2.0 mm. Texture of upper and lower surfaces: Glabrous. Color of inner surface: NN155D with 145D at base. Color of outer surface: NN155D with an overlay of 70A to 70B and 145D at base.

*Pedicle.*—Strength: Strong. Aspect: Erect to approximately 45° from vertical. Length: Approximately 5.0 mm. Diameter: Approximately 1.0 mm. Texture: Densely pubescent with short appressed hairs. Color: 187A.

*Reproductive organs.*—Androecium quantity: 5 per floret. Stamen length; Approximately 5.0 mm, lower 1.0 mm adnate to tube. Anther shape: Oblong. Anther length: Approximately 2.0 mm. Anther color: 70A, transitions to 200B after dehiscence. Filament length of free portion: Approximately 2.0 mm. Filament color: NN155D tinted with N75A. Pollen amount: Moderate. Pollen color: 155D. Gynoecium quantity: 1 per floret. Pistil length: Approximately 1.3 cm. Stigma shape: Bifurcate. Stigma length: Approximately 3.0 mm. Stigma color: N75A. Style length: Approximately 6.0 mm. Style color: NN155D tinted with N75A. Ovary length: Approximately 4.0 mm. Ovary color: 145C.

Seed and fruit production: Neither seed nor fruit production has been observed.

Disease and pest resistance: No particular resistance or susceptibility to other diseases or insects noted to date.

What is claimed is:

1. A new and distinct cultivar of *Eutrochium* plant named 'FLOREUPRE1', substantially as herein illustrated and described.

* * * * *